United States Patent [19]

Mayer et al.

[11] Patent Number: 4,997,368

[45] Date of Patent: Mar. 5, 1991

[54] ORAL MEASURING DEVICE

[76] Inventors: Norman M. Mayer, 106 SW. Greenway Dr., Greensboro, N.C. 27403; Joseph L. Miller, 1903 Downing St., Greensboro, N.C. 27410

[21] Appl. No.: 492,541

[22] Filed: Mar. 12, 1990

[51] Int. Cl.⁵ ............................................. A61C 19/04
[52] U.S. Cl. ........................................ 433/72; 33/514
[58] Field of Search ................. 433/72, 140; 33/513, 33/514

[56] References Cited

U.S. PATENT DOCUMENTS

| | | | |
|---|---|---|---|
| 90,705 | 6/1869 | Von Bonhorst | 33/514 |
| 527,235 | 10/1894 | Carpi | 128/12 |
| 1,348,861 | 8/1920 | Frye, Jr. | 33/562 |
| 1,649,664 | 11/1927 | Carter | 33/514 |
| 1,800,714 | 4/1931 | Clapp | 33/513 |
| 2,846,772 | 8/1958 | Strausser | 33/342 |
| 3,080,654 | 3/1963 | White | 433/140 |
| 3,722,101 | 3/1973 | Via, Jr. | 433/140 |
| 4,624,639 | 11/1986 | Wong | 433/72 |
| 4,741,110 | 5/1988 | Maykel | 33/162 |

*Primary Examiner*—Gene Mancene
*Assistant Examiner*—Michael Lynch

[57] ABSTRACT

An oral measuring device is presented which is formed from plastic or other lightweight substance for insertion in the mouth between the front teeth. The device includes a series of top and bottom arcuately shaped grooves from receiving the teeth. Once the insert has been positioned as far inwardly into the mouth as possible, indicia along the side of the measuring device provides a readily visible measurement of the oral opening.

11 Claims, 2 Drawing Sheets

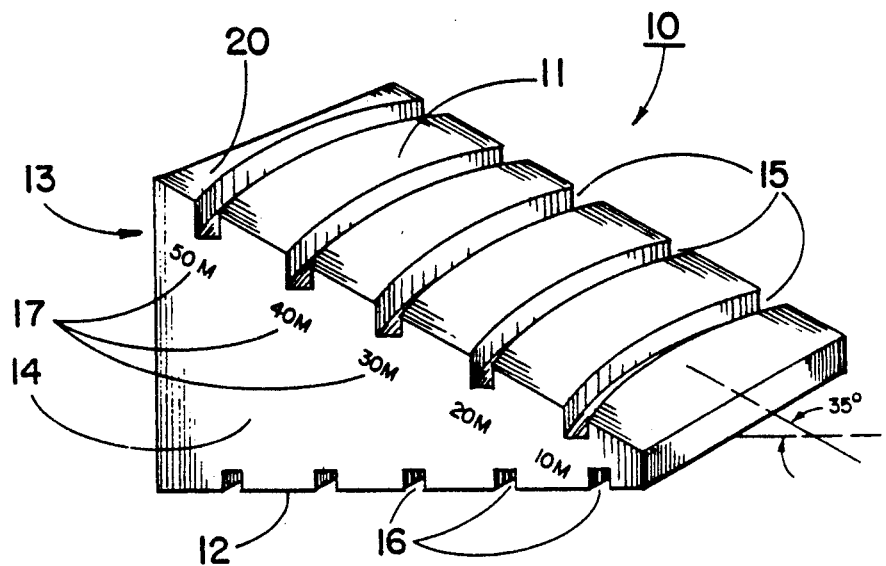
FIG. 1
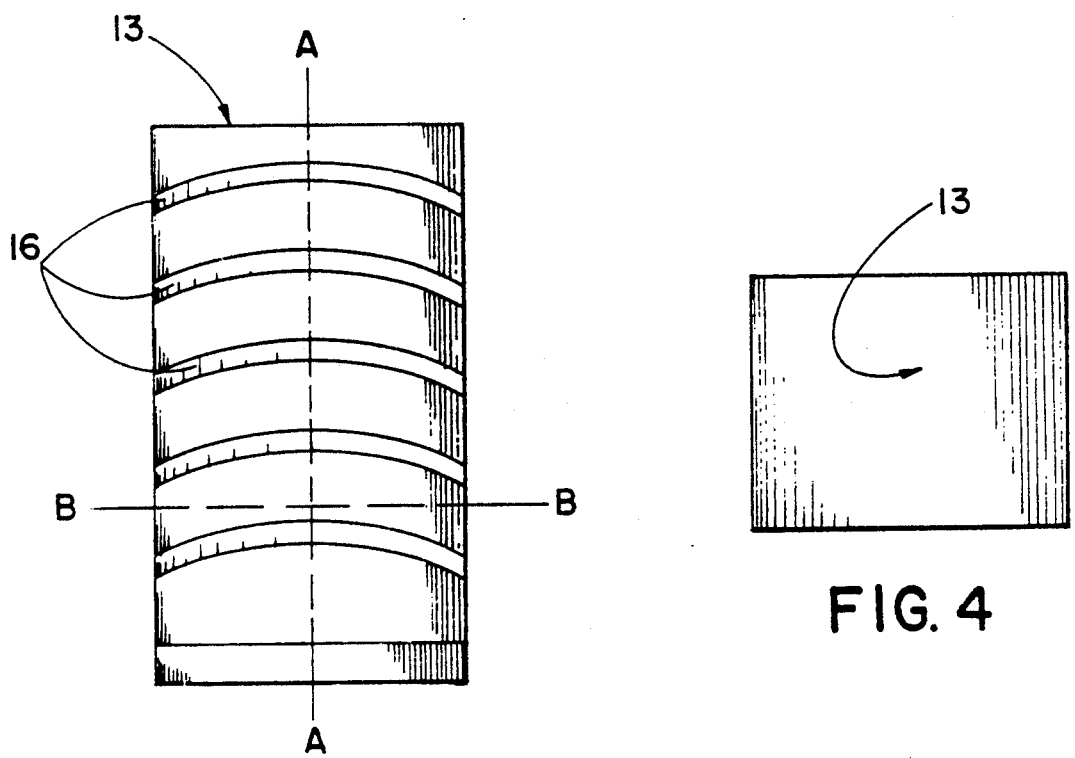
FIG. 3
FIG. 4

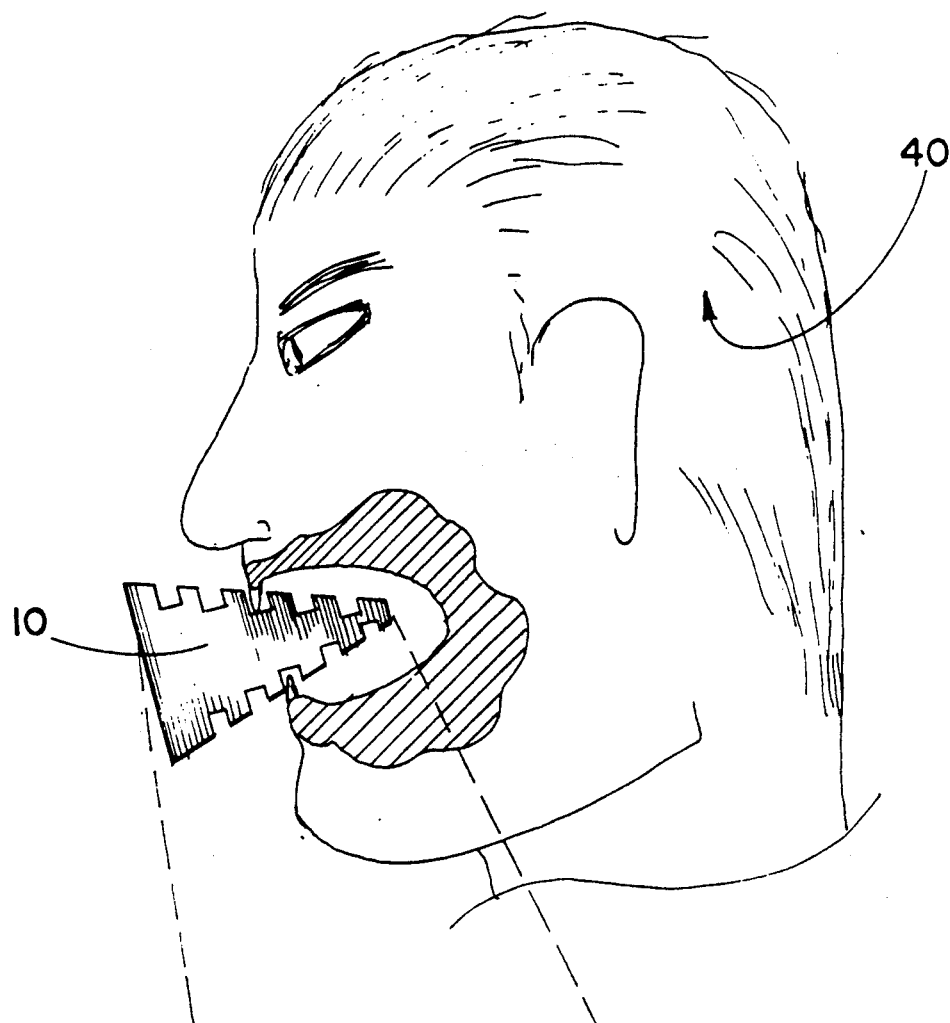
FIG. 2
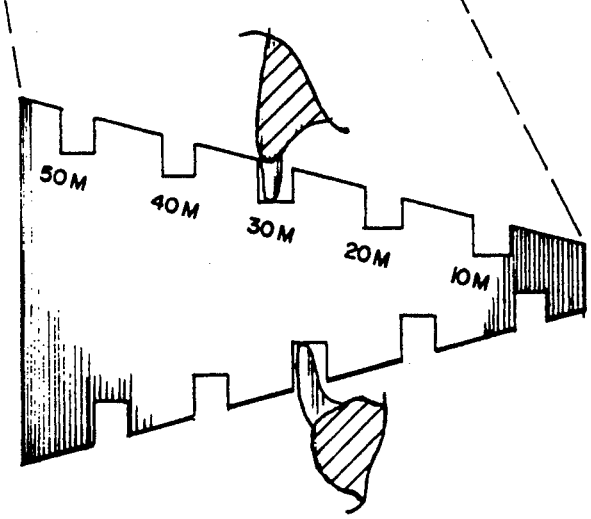

ORAL MEASURING DEVICE

BACKGROUND OF THE INVENTION

1. Field Of The Invention

The present invention pertains to an oral medical instrument and particularly to a measuring device which can be inserted in a patient's mouth to determine the maximum mandible movement or mouth opening achievable by the patient or can be used as a diagnostic tool for measuring the range of motion.

2. Description Of The Prior Art And Objectives Of The Invention

During pre- and post operative examinations of patients who have undergone or may undergo certain facial or oral surgery or have an altered range of motion due to trauma or pathology, it is imperative that the patient be checked or tested to determine the amount of downward lower jaw mobility available, as determined by the size of the mouth opening. In determining the range of motion, surgeons frequently rely on the patient's ability to open his or her mouth without pain as one indicator of the success or nature of the operation or procedure performed. Heretofore, conventional measuring devices such as rulers and other scales have been utilized, but such measuring instruments have not provided the precise data required, nor do they standardize. diagnostic workups. Sometimes inaccuracies resulting from the use of conventional measuring instruments and techniques have proven detrimental in assessing a patient's recovery progress. Hence, a more precise, accurate measuring device and procedure has been needed and it is an objective of the present invention to provide an oral measuring device which can be confidently relied upon for exact mouth opening measurements. This device can also be used by patients to help determine and guide their recovery progress.

It is another objective of the present invention to provide an oral measuring device which is economical to purchase and which can be easily and conveniently inserted between the upper and lower frontal teeth of the patient.

It is yet another objective of the present invention to provide an oral measuring device which has indicia thereon whereby the amount of mouth opening is readily visible to the examiner.

It is still another objective of the present invention to provide an oral measuring device which is substantially wedge-shaped to prevent discomfort and which can be quickly and efficiently employed.

It is yet still another objective of the present invention to provide an oral measuring device which includes a series of notches therealong which will provide a detent for the teeth.

Various other objectives and advantages of the present invention become apparent to those skilled in the art as a more detailed description is presented below.

SUMMARY OF THE INVENTION

The aforesaid and other objectives are realized by providing an oral measuring insert device having biased top and bottom surfaces which can be directed into the mouth between the frontal upper and lower teeth to measure the opening of the mouth. The device may be formed from a lightweight, disposable plastic having arcuate grooves positioned within the upper and lower surfaces providing detents for the teeth. Numerical indicia is placed along the side of the insert to allow the examiner to quickly determine the degree of movement the mandible has undergone at maximum insertion. Various sizes of the insert may be manufactured and made available for different mouth sizes such as for example with young children, older children or adults.

BRIEF DESCRIPTION OF THE DRAWINGS

FIG. 1 demonstrates in perspective fashion an oral insert measuring device of the present invention;

FIG. 2 illustrates the insert in place in the mouth of a patient;

FIG. 3 depicts a bottom view of the device as seen in FIG. 1; and

FIG. 4 shows a rear elevational view thereof.

DESCRIPTION OF THE PREFERRED EMBODIMENT

The preferred form of the invention is pictured in FIG. 1 and comprises a wedge-shaped insert which includes a biased top and bottom surface. Said diagonal surfaces, which may be disposed at an angle of approximately 35°, along with the side walls are manufactured from a synthetic polymer such as polyethylene and form substantially hollow, wedge-shaped insert. A plurality of transverse, arcuate grooves are positioned in the upper and lower surfaces with the lower grooves being disposed somewhat rearwardly of the upper grooves to thereby create detents to accommodate the normal upper and lower teeth alignment of a patient. Numerical indicia is found along the side of the insert proximate each groove for quick determination of the millimeters of mouth opening obtained by the patient.

DETAILED DESCRIPTION OF THE DRAWINGS AND OPERATION OF THE INVENTION

For a more detailed description of the invention and its operation, turning now to the drawings, FIG. 1 depicts in perspective fashion an oral measuring device comprising a wedge-shaped insert 10 which may be formed from plastic, paper, metal or combinations or other suitable materials. As would be understood, oral insert 10 can be made in a sterilized, disposable form or can be made of conventional materials which can be autoclaved and reused. Insert 10 includes top surface 11 and bottom surface 12 (as better seen in FIG. 3) whereby top surface 11 is disposed on a bias to lower surface 12 at an intersecting angle of top surface 11 to bottom surface 12 of approximately 35° as illustrated in FIG. 1, although other sizes and angles may also be found convenient. The rear end 13 of oral insert 10 is substantially planar as seen in FIG. 4 and insert 10 can be formed with relatively thin walls and consists of a hollow interior to reduce weight and to provide economy in manufacturing. Side wall 14 as shown in FIG. 1 comprises a plurality of numerical indicia 17 which demonstrate, for example in millimeters, the mouth opening achieved. As further seen in FIG. 2, patient 40 illustrates a 30 millimeter oral opening.

In order to accurately examine a patient who has undergone oral or related surgery, and to determine the oral opening that he can currently achieve, insert 10 includes top surface 11 and bottom surface 12 which provide a detent for the frontal teeth. Top surface 11 defines somewhat arcuate grooves 15 as seen in FIG. 3 and also shows grooves 16 which are positioned along the transverse axis B—B of bottom surface 12 to accommodate the normal arcuate curvature of the bottom front teeth. As would be understood from FIG. 1, top surface grooves 15 are positioned slightly in advance of bottom grooves 16 along longitudinal axis A—A as seen in FIG. 3 to accommodate a patient's normal overbite. Arcuate grooves 15, 16 may be approximately 1-2 millimeters in depth.

Insert 10 may be molded from resilient plastics or other suitable materials to include top surface grooves 15 and lower surface grooves 16 each of which provides a detent for the teeth as seen in FIG. 2 to insure accurate comparisons and measurements of the patient's recovery process.

The illustrations and examples provided herein are for explanatory purposes and are not intended to limit the scope of the appended claims.

We claim:

1. A device to measure maximum mandible movement comprising: an insert, said insert for placement between the upper and lower front teeth, said insert having a pair of teeth contacting surfaces, one of said pair of surfaces being biased to the other of said surfaces, and one of said teeth contacting surfaces defining an arcuate receiving groove.

2. A device as claimed in claim 1 wherein said insert comprising a wedge-shaped member.

3. A device as claimed in claim 1 wherein said groove is transversely positioned on said insert.

4. A device as claimed in claim 1 wherein said insert is formed from a synthetic polymer.

5. A device as claimed in claim 1 wherein both of said teeth contacting surfaces define receiving grooves.

6. A device as claimed in claim 1 and including indicia, said indicia positioned on said insert proximate said groove.

7. An oral measuring device comprising: an insert, said insert having a top and a bottom surface, said top surface being disposed on a bias to said bottom surface, said top and said bottom surfaces each defining an arcuate receiving groove, said top and said bottom surfaces for receiving upper and lower teeth in said arcuate grooves for determining the opening between the upper and lower jaws.

8. A device as claimed in claim 7 wherein said insert includes numerical indicia thereon.

9. A device as claimed in claim 7 wherein said upper and said lower surfaces define a plurality of receiving grooves.

10. A device as claimed in claim 9 wherein said arcuate grooves are transversely positioned on said surfaces.

11. A device as claimed in claim 9 wherein said upper surface grooves are longitudinally advanced of said lower surface grooves.

* * * * *